United States Patent [19]
White et al.

[11] Patent Number: 5,891,618
[45] Date of Patent: *Apr. 6, 1999

[54] METHOD FOR QUANTIFYING LBP IN BODY FLUIDS

[75] Inventors: Mark Leslie White, Antioch; Stephen Fitzhugh Carroll, Walnut Creek; Jeremy Kam-kuen Ma, San Ramon, all of Calif.

[73] Assignee: XOMA Corporation, Berkeley, Calif.

[*] Notice: The term of this patent shall not extend beyond the expiration date of Pat. Nos. 5,484,705 and 5,804,367.

[21] Appl. No.: 779,400

[22] Filed: Jan. 7, 1997

Related U.S. Application Data

[63] Continuation-in-part of Ser. No. 377,391, Jan. 24, 1995, Pat. No. 5,804,367, which is a continuation-in-part of Ser. No. 186,811, Jan. 24, 1994, Pat. No. 5,484,705.

[51] Int. Cl.$^6$ .................................................. G01N 33/53
[52] U.S. Cl. ................................ 435/4; 435/7.1; 436/536; 530/387.1; 530/388.25; 530/389.3
[58] Field of Search ..................... 435/7.1, 4; 436/536; 530/387.1, 388.25, 389.3

[56] References Cited

U.S. PATENT DOCUMENTS

| | | |
|---|---|---|
| 5,245,013 | 9/1993 | Ulevitch et al. . |
| 5,310,879 | 5/1994 | Ulevitch . |
| 5,484,705 | 1/1996 | White . |

FOREIGN PATENT DOCUMENTS

| | | |
|---|---|---|
| WO 91/01639 | 2/1991 | WIPO . |
| WO 93/06228 | 4/1993 | WIPO . |
| WO 94/21280 | 9/1994 | WIPO . |
| WO 94/25476 | 11/1994 | WIPO . |
| WO 95/00641 | 1/1995 | WIPO . |
| WO 95/02414 | 1/1995 | WIPO . |

*Primary Examiner*—Toni R. Scheiner
*Assistant Examiner*—Nancy A. Johnson
*Attorney, Agent, or Firm*—Marshall, O 'Toole, Gerstein, Murray & Borun

[57] ABSTRACT

The present invention provides a method for quantifying the presence of extracellular LBP in body fluids including blood in a subject comprising conducting an LBP immunoassay on plasma obtained from said subject.

11 Claims, 5 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1443 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 1..1443

(ix) FEATURE:
    (A) NAME/KEY: mat_peptide
    (B) LOCATION: 76..1443

(ix) FEATURE:
    (A) NAME/KEY: misc_feature
    (D) OTHER INFORMATION: "rLBP"

(xi) SEQUENCE DESCRIPTION: SEQ ID NO:1:

```
ATG  GGG  GCC  TTG  GCC  AGA  GCC  CTG  CCG  TCC  ATA  CTG  CTG  GCA  TTG  CTG      48
Met  Gly  Ala  Leu  Ala  Arg  Ala  Leu  Pro  Ser  Ile  Leu  Leu  Ala  Leu  Leu
-25            -20                      -15                           -10

CTT  ACG  TCC  ACC  CCA  GAG  GCT  CTG  GGT  GCC  AAC  CCC  GGC  TTG  GTC  GCC      96
Leu  Thr  Ser  Thr  Pro  Glu  Ala  Leu  Gly  Ala  Asn  Pro  Gly  Leu  Val  Ala
                    -5                        1                    5

AGG  ATC  ACC  GAC  AAG  GGA  CTG  CAG  TAT  GCG  GCC  CAG  GAG  GGG  CTA  TTG     144
Arg  Ile  Thr  Asp  Lys  Gly  Leu  Gln  Tyr  Ala  Ala  Gln  Glu  Gly  Leu  Leu
          10                        15                      20

GCT  CTG  CAG  AGT  GAG  CTG  CTC  AGG  ATC  ACG  CTG  CCT  GAC  TTC  ACC  GGG     192
Ala  Leu  Gln  Ser  Glu  Leu  Leu  Arg  Ile  Thr  Leu  Pro  Asp  Phe  Thr  Gly
          25                        30                      35

GAC  TTG  AGG  ATC  CCC  CAC  GTC  GGC  CGT  GGG  CGC  TAT  GAG  TTC  CAC  AGC     240
Asp  Leu  Arg  Ile  Pro  His  Val  Gly  Arg  Gly  Arg  Tyr  Glu  Phe  His  Ser
40                       45                       50                       55

CTG  AAC  ATC  CAC  AGC  TGT  GAG  CTG  CTT  CAC  TCT  GCG  CTG  AGG  CCT  GTC     288
Leu  Asn  Ile  His  Ser  Cys  Glu  Leu  Leu  His  Ser  Ala  Leu  Arg  Pro  Val
                    60                       65                       70

CCT  GGC  CAG  GGC  CTG  AGT  CTC  AGC  ATC  TCC  GAC  TCC  TCC  ATC  CGG  GTC     336
Pro  Gly  Gln  Gly  Leu  Ser  Leu  Ser  Ile  Ser  Asp  Ser  Ser  Ile  Arg  Val
               75                       80                       85

CAG  GGC  AGG  TGG  AAG  GTG  CGC  AAG  TCA  TTC  TTC  AAA  CTA  CAG  GGC  TCC     384
Gln  Gly  Arg  Trp  Lys  Val  Arg  Lys  Ser  Phe  Phe  Lys  Leu  Gln  Gly  Ser
          90                       95                       100

TTT  GAT  GTC  AGT  GTC  AAG  GGC  ATC  AGC  ATT  TCG  GTC  AAC  CTC  CTG  TTG     432
Phe  Asp  Val  Ser  Val  Lys  Gly  Ile  Ser  Ile  Ser  Val  Asn  Leu  Leu  Leu
     105                      110                      115

GGC  AGC  GAG  TCC  TCC  GGG  AGG  CCC  ACA  GTT  ACT  GCC  TCC  AGC  TGC  AGC     480
Gly  Ser  Glu  Ser  Ser  Gly  Arg  Pro  Thr  Val  Thr  Ala  Ser  Ser  Cys  Ser
120                      125                      130                      135

AGT  GAC  ATC  GCT  GAC  GTG  GAG  GTG  GAC  ATG  TCG  GGA  GAC  TTG  GGG  TGG     528
Ser  Asp  Ile  Ala  Asp  Val  Glu  Val  Asp  Met  Ser  Gly  Asp  Leu  Gly  Trp
                    140                      145                      150

CTG  TTG  AAC  CTC  TTC  CAC  AAC  CAG  ATT  GAG  TCC  AAG  TTC  CAG  AAA  GTA     576
Leu  Leu  Asn  Leu  Phe  His  Asn  Gln  Ile  Glu  Ser  Lys  Phe  Gln  Lys  Val
               155                      160                      165

CTG  GAG  AGC  AGG  ATT  TGC  GAA  ATG  ATC  CAG  AAA  TCG  GTG  TCC  TCC  GAT     624
Leu  Glu  Ser  Arg  Ile  Cys  Glu  Met  Ile  Gln  Lys  Ser  Val  Ser  Ser  Asp
          170                      175                      180

CTA  CAG  CCT  TAT  CTC  CAA  ACT  CTG  CCA  GTT  ACA  ACA  GAG  ATT  GAC  AGT     672
Leu  Gln  Pro  Tyr  Leu  Gln  Thr  Leu  Pro  Val  Thr  Thr  Glu  Ile  Asp  Ser
     185                      190                      195

TTC  GCC  GAC  ATT  GAT  TAT  AGC  TTA  GTG  GAA  GCC  CCT  CGG  GCA  ACA  GCC     720
Phe  Ala  Asp  Ile  Asp  Tyr  Ser  Leu  Val  Glu  Ala  Pro  Arg  Ala  Thr  Ala
200                      205                      210                      215

CAG  ATG  CTG  GAG  GTG  ATG  TTT  AAG  GGT  GAA  ATC  TTT  CAT  CGT  AAC  CAC     768
Gln  Met  Leu  Glu  Val  Met  Phe  Lys  Gly  Glu  Ile  Phe  His  Arg  Asn  His
                    220                      225                      230

CGT  TCT  CCA  GTT  ACC  CTC  CTT  GCT  GCA  GTC  ATG  AGC  CTT  CCT  GAG  GAA     816
Arg  Ser  Pro  Val  Thr  Leu  Leu  Ala  Ala  Val  Met  Ser  Leu  Pro  Glu  Glu
               235                      240                      245

CAC  AAC  AAA  ATG  GTC  TAC  TTT  GCC  ATC  TCG  GAT  TAT  GTC  TTC  AAC  ACG     864
His  Asn  Lys  Met  Val  Tyr  Phe  Ala  Ile  Ser  Asp  Tyr  Val  Phe  Asn  Thr
```

-continued

|     |     |     | 250 |     |     |     |     | 255 |     |     |     |     | 260 |     |     |      |
|-----|-----|-----|-----|-----|-----|-----|-----|-----|-----|-----|-----|-----|-----|-----|-----|------|
| GCC | AGC | CTG | GTT | TAT | CAT | GAG | GAA | GGA | TAT | CTG | AAC | TTC | TCC | ATC | ACA | 912  |
| Ala | Ser | Leu | Val | Tyr | His | Glu | Glu | Gly | Tyr | Leu | Asn | Phe | Ser | Ile | Thr |      |
|     | 265 |     |     |     |     | 270 |     |     |     |     | 275 |     |     |     |     |      |
| GAT | GAG | ATG | ATA | CCG | CCT | GAC | TCT | AAT | ATC | CGA | CTG | ACC | ACC | AAG | TCC | 960  |
| Asp | Glu | Met | Ile | Pro | Pro | Asp | Ser | Asn | Ile | Arg | Leu | Thr | Thr | Lys | Ser |      |
| 280 |     |     |     |     | 285 |     |     |     |     | 290 |     |     |     |     | 295 |      |
| TTC | CGA | CCC | TTC | GTC | CCA | CGG | TTA | GCC | AGG | CTC | TAC | CCC | AAC | ATG | AAC | 1008 |
| Phe | Arg | Pro | Phe | Val | Pro | Arg | Leu | Ala | Arg | Leu | Tyr | Pro | Asn | Met | Asn |      |
|     |     |     |     | 300 |     |     |     |     | 305 |     |     |     |     | 310 |     |      |
| CTG | GAA | CTC | CAG | GGA | TCA | GTG | CCC | TCT | GCT | CCG | CTC | CTG | AAC | TTC | AGC | 1056 |
| Leu | Glu | Leu | Gln | Gly | Ser | Val | Pro | Ser | Ala | Pro | Leu | Leu | Asn | Phe | Ser |      |
|     |     |     | 315 |     |     |     |     | 320 |     |     |     |     | 325 |     |     |      |
| CCT | GGG | AAT | CTG | TCT | GTG | GAC | CCC | TAT | ATG | GAG | ATA | GAT | GCC | TTT | GTG | 1104 |
| Pro | Gly | Asn | Leu | Ser | Val | Asp | Pro | Tyr | Met | Glu | Ile | Asp | Ala | Phe | Val |      |
|     |     | 330 |     |     |     |     | 335 |     |     |     |     | 340 |     |     |     |      |
| CTC | CTG | CCC | AGC | TCC | AGC | AAG | GAG | CCT | GTC | TTC | CGG | CTC | AGT | GTG | GCC | 1152 |
| Leu | Leu | Pro | Ser | Ser | Ser | Lys | Glu | Pro | Val | Phe | Arg | Leu | Ser | Val | Ala |      |
|     |     | 345 |     |     |     |     | 350 |     |     |     |     | 355 |     |     |     |      |
| ACT | AAT | GTG | TCC | GCC | ACC | TTG | ACC | TTC | AAT | ACC | AGC | AAG | ATC | ACT | GGG | 1200 |
| Thr | Asn | Val | Ser | Ala | Thr | Leu | Thr | Phe | Asn | Thr | Ser | Lys | Ile | Thr | Gly |      |
| 360 |     |     |     |     | 365 |     |     |     |     | 370 |     |     |     |     | 375 |      |
| TTC | CTG | AAG | CCA | GGA | AAG | GTA | AAA | GTG | GAA | CTG | AAA | GAA | TCC | AAA | GTT | 1248 |
| Phe | Leu | Lys | Pro | Gly | Lys | Val | Lys | Val | Glu | Leu | Lys | Glu | Ser | Lys | Val |      |
|     |     |     |     | 380 |     |     |     |     | 385 |     |     |     |     | 390 |     |      |
| GGA | CTA | TTC | AAT | GCA | GAG | CTG | TTG | GAA | GCG | CTC | CTC | AAC | TAT | TAC | ATC | 1296 |
| Gly | Leu | Phe | Asn | Ala | Glu | Leu | Leu | Glu | Ala | Leu | Leu | Asn | Tyr | Tyr | Ile |      |
|     |     |     | 395 |     |     |     |     | 400 |     |     |     |     | 405 |     |     |      |
| CTT | AAC | ACC | TTC | TAC | CCC | AAG | TTC | AAT | GAT | AAG | TTG | GCC | GAA | GGC | TTC | 1344 |
| Leu | Asn | Thr | Phe | Tyr | Pro | Lys | Phe | Asn | Asp | Lys | Leu | Ala | Glu | Gly | Phe |      |
|     |     | 410 |     |     |     |     | 415 |     |     |     |     | 420 |     |     |     |      |
| CCC | CTT | CCT | CTG | CTG | AAG | CGT | GTT | CAG | CTC | TAC | GAC | CTT | GGG | CTG | CAG | 1392 |
| Pro | Leu | Pro | Leu | Leu | Lys | Arg | Val | Gln | Leu | Tyr | Asp | Leu | Gly | Leu | Gln |      |
|     |     | 425 |     |     |     |     | 430 |     |     |     |     | 435 |     |     |     |      |
| ATC | CAT | AAG | GAC | TTC | CTG | TTC | TTG | GGT | GCC | AAT | GTC | CAA | TAC | ATG | AGA | 1440 |
| Ile | His | Lys | Asp | Phe | Leu | Phe | Leu | Gly | Ala | Asn | Val | Gln | Tyr | Met | Arg |      |
| 440 |     |     |     |     | 445 |     |     |     |     | 450 |     |     |     |     | 455 |      |
| GTT |     |     |     |     |     |     |     |     |     |     |     |     |     |     |     | 1443 |
| Val |     |     |     |     |     |     |     |     |     |     |     |     |     |     |     |      |

( 2 ) INFORMATION FOR SEQ ID NO:2:

( i ) SEQUENCE CHARACTERISTICS:
        ( A ) LENGTH: 481 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( D ) OTHER INFORMATION: "rLBP"

( x i ) SEQUENCE DESCRIPTION: SEQ ID NO:2:

| Met | Gly | Ala | Leu | Ala | Arg | Ala | Leu | Pro | Ser | Ile | Leu | Leu | Ala | Leu | Leu |
|-----|-----|-----|-----|-----|-----|-----|-----|-----|-----|-----|-----|-----|-----|-----|-----|
| -25 |     |     |     |     | -20 |     |     |     |     | -15 |     |     |     |     | -10 |

| Leu | Thr | Ser | Thr | Pro | Glu | Ala | Leu | Gly | Ala | Asn | Pro | Gly | Leu | Val | Ala |
|-----|-----|-----|-----|-----|-----|-----|-----|-----|-----|-----|-----|-----|-----|-----|-----|
|     |     |     |     | -5  |     |     |     |     | 1   |     |     |     |     | 5   |     |

| Arg | Ile | Thr | Asp | Lys | Gly | Leu | Gln | Tyr | Ala | Ala | Gln | Glu | Gly | Leu | Leu |
|-----|-----|-----|-----|-----|-----|-----|-----|-----|-----|-----|-----|-----|-----|-----|-----|
|     |     | 10  |     |     |     |     | 15  |     |     |     |     | 20  |     |     |     |

| Ala | Leu | Gln | Ser | Glu | Leu | Leu | Arg | Ile | Thr | Leu | Pro | Asp | Phe | Thr | Gly |
|-----|-----|-----|-----|-----|-----|-----|-----|-----|-----|-----|-----|-----|-----|-----|-----|
|     |     | 25  |     |     |     |     | 30  |     |     |     |     | 35  |     |     |     |

Asp Leu Arg Ile Pro His Val Gly Arg Gly Arg Tyr Glu Phe His Ser
40                      45                  50                  55

Leu Asn Ile His Ser Cys Glu Leu Leu His Ser Ala Leu Arg Pro Val
                    60              65                  70

Pro Gly Gln Gly Leu Ser Leu Ser Ile Ser Asp Ser Ser Ile Arg Val
            75              80                  85

Gln Gly Arg Trp Lys Val Arg Lys Ser Phe Phe Lys Leu Gln Gly Ser
            90              95              100

Phe Asp Val Ser Val Lys Gly Ile Ser Ile Ser Val Asn Leu Leu Leu
        105             110             115

Gly Ser Glu Ser Ser Gly Arg Pro Thr Val Thr Ala Ser Ser Cys Ser
120             125             130                         135

Ser Asp Ile Ala Asp Val Glu Val Asp Met Ser Gly Asp Leu Gly Trp
                140             145                     150

Leu Leu Asn Leu Phe His Asn Gln Ile Glu Ser Lys Phe Gln Lys Val
            155             160             165

Leu Glu Ser Arg Ile Cys Glu Met Ile Gln Lys Ser Val Ser Ser Asp
        170             175             180

Leu Gln Pro Tyr Leu Gln Thr Leu Pro Val Thr Thr Glu Ile Asp Ser
        185             190             195

Phe Ala Asp Ile Asp Tyr Ser Leu Val Glu Ala Pro Arg Ala Thr Ala
200             205             210                         215

Gln Met Leu Glu Val Met Phe Lys Gly Glu Ile Phe His Arg Asn His
                220             225             230

Arg Ser Pro Val Thr Leu Leu Ala Ala Val Met Ser Leu Pro Glu Glu
            235             240             245

His Asn Lys Met Val Tyr Phe Ala Ile Ser Asp Tyr Val Phe Asn Thr
            250             255             260

Ala Ser Leu Val Tyr His Glu Glu Gly Tyr Leu Asn Phe Ser Ile Thr
            265             270             275

Asp Glu Met Ile Pro Pro Asp Ser Asn Ile Arg Leu Thr Thr Lys Ser
280             285             290                         295

Phe Arg Pro Phe Val Pro Arg Leu Ala Arg Leu Tyr Pro Asn Met Asn
                300             305             310

Leu Glu Leu Gln Gly Ser Val Pro Ser Ala Pro Leu Leu Asn Phe Ser
            315             320             325

Pro Gly Asn Leu Ser Val Asp Pro Tyr Met Glu Ile Asp Ala Phe Val
            330             335             340

Leu Leu Pro Ser Ser Ser Lys Glu Pro Val Phe Arg Leu Ser Val Ala
            345             350             355

Thr Asn Val Ser Ala Thr Leu Thr Phe Asn Thr Ser Lys Ile Thr Gly
360             365             370                         375

Phe Leu Lys Pro Gly Lys Val Lys Val Glu Leu Lys Glu Ser Lys Val
                380             385             390

Gly Leu Phe Asn Ala Glu Leu Leu Glu Ala Leu Leu Asn Tyr Tyr Ile
            395             400             405

Leu Asn Thr Phe Tyr Pro Lys Phe Asn Asp Lys Leu Ala Glu Gly Phe
            410             415             420

Pro Leu Pro Leu Leu Lys Arg Val Gln Leu Tyr Asp Leu Gly Leu Gln
            425             430             435

Ile His Lys Asp Phe Leu Phe Leu Gly Ala Asn Val Gln Tyr Met Arg
440             445             450                         455

Val (2) INFORMATION FOR SEQ ID NO:3:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..591

(ix) FEATURE:
        (A) NAME/KEY: misc_feature
        (D) OTHER INFORMATION: "rLBP25"

(xi) SEQUENCE DESCRIPTION: SEQ ID NO:3:

```
GCC  AAC  CCC  GGC  TTG  GTC  GCC  AGG  ATC  ACC  GAC  AAG  GGA  CTG  CAG  TAT      48
Ala  Asn  Pro  Gly  Leu  Val  Ala  Arg  Ile  Thr  Asp  Lys  Gly  Leu  Gln  Tyr
 1              5                        10                       15

GCG  GCC  CAG  GAG  GGG  CTA  TTG  GCT  CTG  CAG  AGT  GAG  CTG  CTC  AGG  ATC      96
Ala  Ala  Gln  Glu  Gly  Leu  Leu  Ala  Leu  Gln  Ser  Glu  Leu  Leu  Arg  Ile
           20                        25                       30

ACG  CTG  CCT  GAC  TTC  ACC  GGG  GAC  TTG  AGG  ATC  CCC  CAC  GTC  GGC  CGT     144
Thr  Leu  Pro  Asp  Phe  Thr  Gly  Asp  Leu  Arg  Ile  Pro  His  Val  Gly  Arg
                35                        40                       45

GGG  CGC  TAT  GAG  TTC  CAC  AGC  CTG  AAC  ATC  CAC  AGC  TGT  GAG  CTG  CTT     192
Gly  Arg  Tyr  Glu  Phe  His  Ser  Leu  Asn  Ile  His  Ser  Cys  Glu  Leu  Leu
           50                        55                       60

CAC  TCT  GCG  CTG  AGG  CCT  GTC  CCT  GGC  CAG  GGC  CTG  AGT  CTC  AGC  ATC     240
His  Ser  Ala  Leu  Arg  Pro  Val  Pro  Gly  Gln  Gly  Leu  Ser  Leu  Ser  Ile
 65                       70                        75                       80

TCC  GAC  TCC  TCC  ATC  CGG  GTC  CAG  GGC  AGG  TGG  AAG  GTG  CGC  AAG  TCA     288
Ser  Asp  Ser  Ser  Ile  Arg  Val  Gln  Gly  Arg  Trp  Lys  Val  Arg  Lys  Ser
                     85                       90                       95

TTC  TTC  AAA  CTA  CAG  GGC  TCC  TTT  GAT  GTC  AGT  GTC  AAG  GGC  ATC  AGC     336
Phe  Phe  Lys  Leu  Gln  Gly  Ser  Phe  Asp  Val  Ser  Val  Lys  Gly  Ile  Ser
                100                       105                      110

ATT  TCG  GTC  AAC  CTC  CTG  TTG  GGC  AGC  GAG  TCC  TCC  GGG  AGG  CCC  ACA     384
Ile  Ser  Val  Asn  Leu  Leu  Leu  Gly  Ser  Glu  Ser  Ser  Gly  Arg  Pro  Thr
           115                      120                      125

GTT  ACT  GCC  TCC  AGC  TGC  AGC  AGT  GAC  ATC  GCT  GAC  GTG  GAG  GTG  GAC     432
Val  Thr  Ala  Ser  Ser  Cys  Ser  Ser  Asp  Ile  Ala  Asp  Val  Glu  Val  Asp
           130                      135                      140

ATG  TCG  GGA  GAC  TTG  GGG  TGG  CTG  TTG  AAC  CTC  TTC  CAC  AAC  CAG  ATT     480
Met  Ser  Gly  Asp  Leu  Gly  Trp  Leu  Leu  Asn  Leu  Phe  His  Asn  Gln  Ile
145                      150                      155                      160

GAG  TCC  AAG  TTC  CAG  AAA  GTA  CTG  GAG  AGC  AGG  ATT  TGC  GAA  ATG  ATC     528
Glu  Ser  Lys  Phe  Gln  Lys  Val  Leu  Glu  Ser  Arg  Ile  Cys  Glu  Met  Ile
                165                      170                      175

CAG  AAA  TCG  GTG  TCC  TCC  GAT  CTA  CAG  CCT  TAT  CTC  CAA  ACT  CTG  CCA     576
Gln  Lys  Ser  Val  Ser  Ser  Asp  Leu  Gln  Pro  Tyr  Leu  Gln  Thr  Leu  Pro
                180                      185                      190

GTT  ACA  ACA  GAG  ATT                                                             591
Val  Thr  Thr  Glu  Ile
                195
```

(2) INFORMATION FOR SEQ ID NO:4:

(i) SEQUENCE CHARACTERISTICS:
        (A) LENGTH: 197 amino acids
        (B) TYPE: amino acid -continued ( D ) TOPOLOGY: linear ( i i ) MOLECULE TYPE: protein ( i x ) FEATURE:
    ( A ) NAME/KEY: misc_feature
    ( D ) OTHER INFORMATION: "rLBP25"

( x i ) SEQUENCE DESCRIPTION: SEQ ID NO:4:

```
Ala  Asn  Pro  Gly  Leu  Val  Ala  Arg  Ile  Thr  Asp  Lys  Gly  Leu  Gln  Tyr
 1               5                        10                       15
Ala  Ala  Gln  Glu  Gly  Leu  Leu  Ala  Leu  Gln  Ser  Glu  Leu  Leu  Arg  Ile
               20                        25                       30
Thr  Leu  Pro  Asp  Phe  Thr  Gly  Asp  Leu  Arg  Ile  Pro  His  Val  Gly  Arg
               35                        40                  45
Gly  Arg  Tyr  Glu  Phe  His  Ser  Leu  Asn  Ile  His  Ser  Cys  Glu  Leu  Leu
          50                        55                  60
His  Ser  Ala  Leu  Arg  Pro  Val  Pro  Gly  Gln  Gly  Leu  Ser  Leu  Ser  Ile
 65                      70                        75                        80
Ser  Asp  Ser  Ser  Ile  Arg  Val  Gln  Gly  Arg  Trp  Lys  Val  Arg  Lys  Ser
                    85                        90                       95
Phe  Phe  Lys  Leu  Gln  Gly  Ser  Phe  Asp  Val  Ser  Val  Lys  Gly  Ile  Ser
              100                       105                 110
Ile  Ser  Val  Asn  Leu  Leu  Leu  Gly  Ser  Glu  Ser  Ser  Gly  Arg  Pro  Thr
              115                       120                 125
Val  Thr  Ala  Ser  Ser  Cys  Ser  Ser  Asp  Ile  Ala  Asp  Val  Glu  Val  Asp
     130                       135                 140
Met  Ser  Gly  Asp  Leu  Gly  Trp  Leu  Leu  Asn  Leu  Phe  His  Asn  Gln  Ile
145                      150                       155                      160
Glu  Ser  Lys  Phe  Gln  Lys  Val  Leu  Glu  Ser  Arg  Ile  Cys  Glu  Met  Ile
              165                       170                 175
Gln  Lys  Ser  Val  Ser  Ser  Asp  Leu  Gln  Pro  Tyr  Leu  Gln  Thr  Leu  Pro
              180                       185                 190
Val  Thr  Thr  Glu  Ile
              195
```

METHOD FOR QUANTIFYING LBP IN BODY FLUIDS

This application is a continuation-in-part of U.S. Ser. No. 08/377,391 filed Jan. 24, 1995, which issued Sep. 8, 1998 as U.S. Pat. No. 5,804,367 which is in turn a continuation-in-part of U.S. patent application Ser. No. 08/186,811 filed Jan. 24, 1994, which issued Jan. 16, 1996 as U.S. Pat. No. 5,484,705 all of which are incorporated herein by reference.

BACKGROUND OF THE INVENTION

The present invention relates to methods for determination of the presence of Lipopolysaccharide binding protein (LBP) in body fluid samples including blood samples.

Lipopolysaccharide (LPS) is a common component of the outer membrane of Gram-negative bacteria and is responsible for many of the pathologic effects associated with gram-negative bacterial infection and endotoxemia. Because of the association between bacterial infection and sepsis, attempts have been made to correlate serum/plasma levels of endotoxin with disease. Typically, endotoxin levels have been measured using the Limulus amebocyte lysate (LAL) assay, in which endotoxin initiates a coagulation cascade that can be measured physically, turbidimetrically, or spectrophotometrically, Despite these attempts, however, no reliable correlations between endotoxin levels and sepsis severity or outcome have been identified. This is most likely due to the fact that (i) endotoxin levels in septic patients are very low (>10 pg/L), several serum proteins interfere with the proteolytic LAL cascade, (iii) endotoxin, once in contact with blood, can be "detoxified" by interaction with a variety of blood components, including high-density lipoprotein (HDL) and low-density lipoprotein (LDL) and (iv) endotoxin from different gram-negative organisms varies in its ability to trigger the LAL cascade. Thus, the absolute levels of endotoxin in a patient sample may not correspond to the actual concentrations of bioactive endotoxin present in vivo.

Two related proteins have been identified in humans and other animals that bind LPS with high affinity. These two proteins, Lipopolysaccharide binding protein (LBP), and bactericidal/permeability increasing protein (BPI) have roughly the same molecular weight and share 45% amino acid homology, yet exhibit distinct physiological differences. LBP is a 60 kD glycoprotein synthesized in the liver, while BPI is found in the azurophilic granules of neutrophils. LBP is found in the serum of normal humans at levels of 5–10 µg/mL but can reach levels of 50–100 µg/mL in septic patients. Schumann et al., *Science,* 249:1429 (1990) disclose the amino acid sequences and encoding cDNA of both human and rabbit LBP. Like BPI, LBP has a binding site for lipid A and binds to the LPS from rough (R-) and smooth (S-) form bacteria. Unlike BPI, LBP does not possess significant bactericidal activity. BPI has been observed to neutralize and inhibit the production of TNF resulting from interaction of LBP with LPS and CD14 on monocytes and macrophages. Marra et al., *J. Immunol.* 148: 532 (1992), Weiss et al., *J. Clin. Invest.* 90: 1122 (1992). In contrast, LBP is observed to enhance LPS-induced TNF production. Wright et al., *Science,* 249:1131 (1990). Thus, in contrast to BPI, LBP has been recognized as an immunostimulatory molecule. See, e.g., Seilhamer, PCT International Application WO 93/06228 which discloses a variant form of LBP which it terms LBP-β. Also of interest to the present invention are Ulevitch, PCT International Application WO 91/01639 which discloses, among other things, anti-LBP antibodies as an anti-sepsis therapeutic agent and U.S. Pat. No. 5,245,013 which relates to LBP and discloses antibodies which immunoreact with a polypeptide having homology to LBP.

LBP has been characterized in the art as an "acute phase protein", that is one of many plasma proteins (such as C-reactive protein, fibrinogen and serum amyloid A) that increase in concentration in response to infectious and non-infectious tissue destructive processes. As such, it would be anticipated that LBP levels would be elevated in samples from patients suffering from a number of autoimmune diseases such as rheumatoid arthritis and lupus erythematosus.

Of interest to the present invention are disclosures related to the assaying of BPI activity in subjects. von der Mohien et al., Abstract, 13th International Symposium on Intensive Care and Emergency Medicine, Brussels (March 1993) discloses the results of assays for serum levels of BPI in patients with gram-negative sepsis and healthy subjects. The abstract disclosed that no BPI was detectable under the conditions of the assay in the serum of healthy subjects while circulating BPI was detected in all septic patients. Also of interest is the disclosure of co-owned and copending U.S. patent application Ser. No. 08/175,276 filed Dec. 29, 1993 which is a continuation-in-part of application Ser. No. 08/125,677 filed Sep. 22, 1993 the disclosures of which are hereby incorporated by reference. Those patent applications disclose that levels of BPI in blood plasma samples correlate with the presence or absence of sepsis while levels of BPI in blood serum samples do not. The patent applications teach that levels of BPI present in serum are not representative of endogenous extracellular levels of BPI in circulating blood while levels of BPI in plasma are.

Also of interest to the present invention are the disclosures of Leturcq et al., Keystone Tahoe Endotoxin Conference, Mar., 1–7, 1992 (Abstract) in which the generation of monoclonal antibodies to human LBP is reported. Also reported is the screening of normal human serum samples for the presence of LBP. LBP levels for normal serum samples were reported to range from 1 µg/mL to 24 µg/mL with an average of 7 µg/mL. Further of interest is the disclosure of Richard Ulevitch at the American Society for Microbiology General Meeting in Atlanta, Ga. May 16–21 (1993) at which data was presented on LBP and soluble CD14 levels in the serum of septic and healthy individuals. The average soluble CD14 and LBP concentrations in the serum of healthy adults were 1 µg/mL and 7 µg/mL respectively. The average soluble CD14 and LBP concentrations in the serum of septic patients were reported to be 2 µg/mL and 55 µg/mL respectively.

Geller et al., *Arch. Surg.,* 128: 22–28 (1993) disclose experiments in which the induction of LBP mRNA was studied in three models known to induce acute phase responses: (1) LPS injection; (2) *Corynebacterium parvum* injection; and (3) turpentine injection. The publication reports that LBP mRNA is induced during hepatic inflammation and suggest that LBP is an acute-phase protein important in regulating the in vivo response to endotoxin.

Gallay et al., *Infect. Immun.,* 61:378–383 (1993) disclose that an acute phase response in mice injected with silver nitrate induced LBP synthesis, and that LBP levels increase approximately 10-fold over normal levels after an acute-phase response.

There exists a desire in the art for methods for determining the exposure of subjects to endotoxin and for distinguishing the effects of exposure to endotoxin from other acute phase physiologic responses. Also desired are methods for diagnosing the presence or severity of gram-negative sepsis in a subject and for predicting the prognosis of a subject suffering from sepsis.

SUMMARY OF THE INVENTION

The present invention provides methods for specifically determining exposure of a subject to endotoxin by assaying for LBP. The invention further provides methods for screening for exposure to gram-negative bacterial endotoxin in an acute phase response in humans by assaying for LBP. Specifically, the method comprises the steps of determining the concentration of LBP in a sample of body fluid from the subject and correlating the concentration of LBP with a standard indicative of the exposure to endotoxin. Such standards can include a subjective standard for a given subject determined by LBP levels of that subject in a pretreatment state such as prior to undergoing surgery. Exposure to endotoxin as a consequence of such surgery can be determined by comparing post-surgical LBP levels with the standard established prior to surgery for that subject. Where access to a pretreatment standard level of LBP is not available for a given individual, objective standards based upon population or subpopulation averages may be applied for comparison. One such standard can be a concentration greater than approximately 15 μg/mL in human plasma or serum, as determined herein for LBP values in subjects suffering from numerous disease states. Subjects exhibiting LBP levels above that standard could presumptively be diagnosed as suffering from exposure to endotoxin while those having levels below that standard would not be. It is clear that alternative standards could be established depending upon the desired sensitivity and selectivity of an assay method and upon the subpopulation in which a given subject falls. For example, standards might be established at different levels for different ages, genders, ethnicities and underlying health conditions of various subpopulations. Moreover, it should be understood that standard levels will differ according to the identity of the particular body fluid which is assayed.

The invention further provides methods for diagnosing the presence or severity of sepsis in a subject comprising the steps of determining the concentration of LBP in a sample of body fluid from the subject and correlating the concentration of LBP with a standard indicative of the presence or severity of sepsis. The invention further provides methods for predicting the prognosis of a subject suffering from sepsis comprising the steps of determining the concentration of LBP in a sample of body fluid from the subject and correlating the concentration of LBP with a standard indicative of the prognosis of a subject suffering from sepsis.

DETAILED DESCRIPTON OF THE INVENTION

Figure 1:
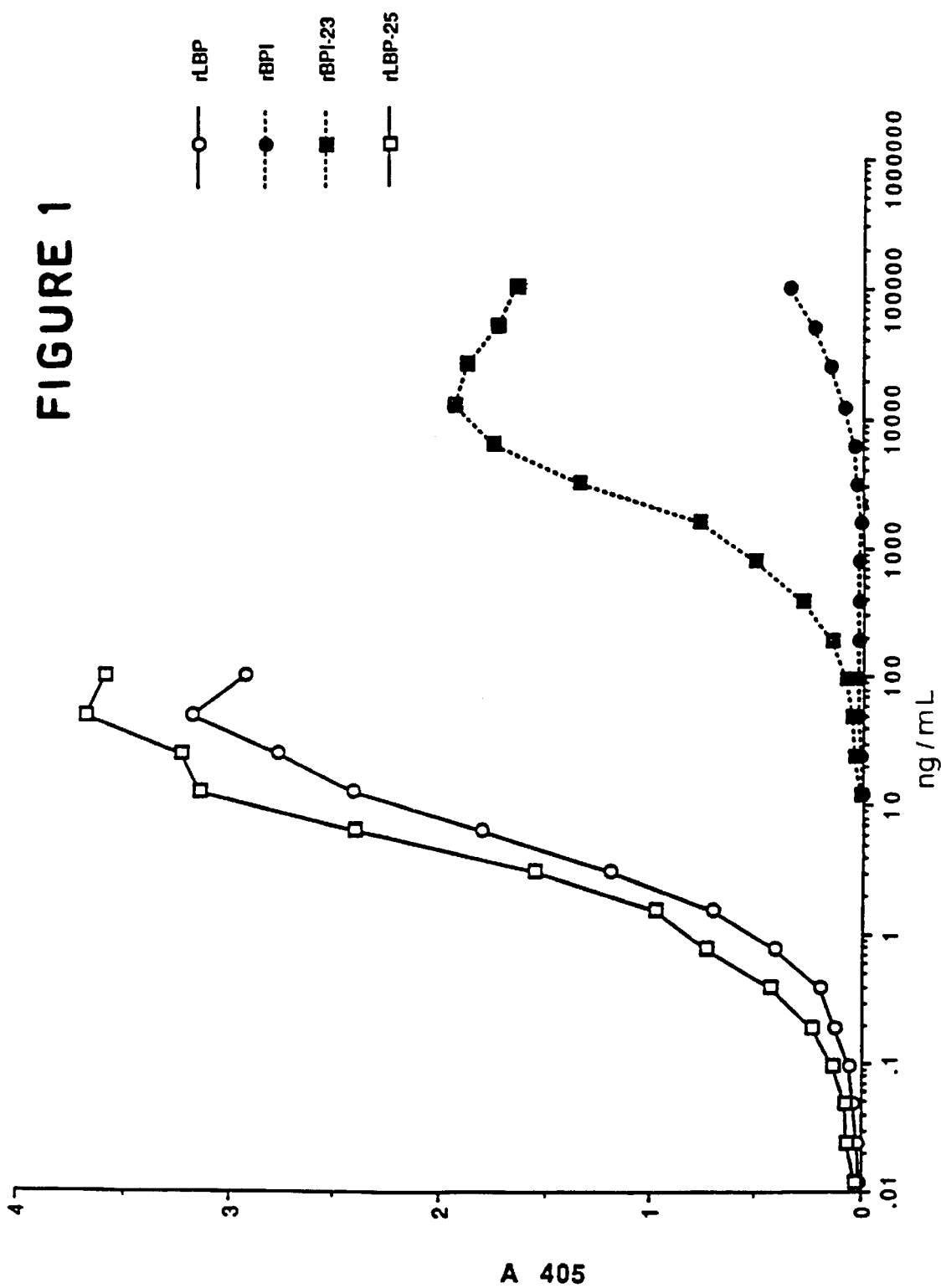
FIG. 1 depicts the dose-response curves for rLBP, rLBP$_{25}$, rBPI and rBPI$_{23}$ in LBP sandwich assays.

The present invention relates to methods for quantifying the presence of LBP in body fluids including blood. While the assay can be used to determine the presence and quantity of LBP which has been administered therapeutically, it is particularly useful for quantifying the presence of endogenous LBP in circulating blood as an indication of exposure of a subject to endotoxin. Moreover, quantifying the presence of LBP is contemplated to be useful in diagnostic and prognostic methods for evaluating gram-negative sepsis patients.

The present invention provides a sandwich ELISA assay for human LBP which exhibits high assay sensitivity, high specificity, and excellent reproducibility. As used herein "LBP" quantitated according to assay methods includes native LBP, recombinant LBP, LBP fragments and analogs as well as other LBP proteins and protein products.

The amino acid and nucleotide sequence of recombinant LBP are set out in co-owned and copending U.S. patent application Ser. No. 08/029,510 filed Jun. 17, 1993 as shown in SEQ ID NOS: 1 and 2 herein. A recombinant LBP amino-terminal fragment is characterized by the amino acid sequence of the first 197 amino acids of the amino-terminus of LBP as set out in SEQ ID NOS: 3 and 4 the production of which is described in co-owned and copending U.S. patent application Ser. No. 08/079,510 filed Jun. 12, 1993 the disclosure of which is incorporated herein. Such LBP protein products may be readily quantified using assays including immunological assays and bioassays in the subnanogram per mL range. Immunological assays capable of quantifying LBP are preferably carried out by enzyme linked immunosorbant (ELISA) sandwich assays but competitive assays and immunological assays utilizing other labelling formats may also be used. Preferred assays of the invention utilize anti-LBP antibodies, including monoclonal antibodies and affinity-purified rabbit polyclonal antibodies. Rabbit polyclonal anti-LBP antibodies may be prepared according to conventional methods using LBP as an immunogen. Non-immunological methods may also be used to assay for LBP. As one example, Ulevitch et al., U.S. Pat. No. 5,245,013 disclose assay methods comprising binding of LBP to LPS and separating the complex by a centrifugation density gradient method. As another example, Geller et al., *Arch. Surg.* 128: 22–28 (1993) disclose LBP bioactivity assays in which IL-6 and TNF upregulation are measured.

Body fluids which can be assayed for the presence of LBP include whole blood with blood serum and blood plasma being preferred. Because LBP is a serum protein it is contemplated that it could be excreted and that analysis of LBP levels in urine may provide diagnostic and prognostic utility. The LBP immunoassays of the invention may also be used to determine the concentration of LBP in other body fluids including, but not limited to lung lavages, vitreous fluid, crevicular fluid, cerebrospinal fluid, saliva, sputum, ascites, amniotic fluid and synovial fluid.

Because LBP has been characterized as an "acute phase protein" it would be expected that LBP levels would be elevated in subjects suffering from autoimmune diseases. As one aspect of the present invention it has been found that LBP levels are not substantially elevated over normal in subjects with malignancies, immune diseases or syndromes, viral conditions and other conditions, such as, specifically, acute lymphoblastic leukemia (ALL), acute graft versus host disease (aGvHD), chronic lymphocytic leukemia (CLL), cutaneous T-cell lymphoma (CTCL), type 1 diabetes, aplastic anemia (AA), Crohn's Disease, psoriasis, rheumatoid arthritis (RA), scleroderma, systemic lupus erythematosus (SLE), pregnancy and acquired immune deficiency syndrome (AIDS). In these patients with a condition not associated with endotoxin and thus not associated with elevated LBP levels, exposure to endotoxin is expected to produce a rise in LBP levels over the normal baseline LBP values for that condition. Thus, an elevation in LBP levels for these and other patient populations, like healthy subjects (i.e., subjects with no evidence of disease), is expected to be diagnostic of an exposure to endotoxin.

The invention thus contemplates use of the LBP assay for distinguishing conditions associated with endotoxin from conditions (either acute phase or non-acute phase) not associated with endotoxin. The invention also contemplates the detection of exposure to endotoxin in healthy subjects or in patients with a condition not associated with endotoxin. The invention further contemplates multiple determinations of LBP levels of a subject over time, either to monitor for potential development of a condition associated with endotoxin or to monitor a subject for the severity or prognosis of a condition associated with endotoxin.

Certain subjects tentatively identified as suffering from gram-negative sepsis but ultimately identified as suffering from gram-positive sepsis also had elevated LBP levels. It is noted that translocation of bacteria and/or endotoxin from the gut into the bloodstream can occur in any infection. Thus, infections due to gram-positive bacteria or fungi may also lead to the presence of endotoxin or gram-negative bacteria in the blood and, therefore elevated levels of LBP.

The present invention is based in part upon the observation that serum and plasma levels of LBP directly correlate with a subject's exposure to biologically active LPS. Moreover, LBP levels appear to correlate with survival in suspected gram-negative sepsis patients. For example, subjects with levels of circulating LBP below 27.3 μg/mL (the median value for 58 subjects suffering from gram-negative sepsis) tended to have a greater 14 day survival than did those subjects with levels of LBP above that median. Further, for example, when a plasma LBP threshold level was set at 46 μg/mL, those subjects having a pretreatment LBP plasma level less than 46 μg/mL had a significantly greater survival rate (p=0.004) over a 27 day period than did those subjects having a pretreatment plasma LBP level greater than 46 μg/mL.

It is further contemplated by the invention that elevated levels of LBP may result from exposure to larger amounts of endotoxin, and may therefore be diagnostic of greater infection and/or endotoxemia severity. Elevated levels of LBP may also be used to indicate the suitability of using antibiotics directed against gram-negative bacteria or other therapeutic agents targeted directly to endotoxin such as BPI or anti-endotoxin antibodies including the monoclonal antibody E5.

Other aspects and advantages of the present invention will be understood upon consideration of the following illustrative examples. Example 1 relates to the preparation of affinity purified rabbit anti-BPI antibodies; Example 2 relates to the biotin labeling of such antibodies; and Example 3 relates to ELISA procedures utilizing such antibodies. Example 4 relates to the comparative immunoreactivity of rLBP, $rLBP_{25}$, rBPI AND $rBPI_{23}$. Example 5 relates to the measurement of rLBP spiked into pooled human plasma; and Example 6 relates to the comparison of LBP levels in human plasma and serum. Example 7 relates to the clinical correlations of endogenous LBP immunoreactivity with sepsis and other disease states in human plasma; and Example 8 relates to the effect of LPS administration on endogenous LBP levels in healthy subjects. Example 9 relates to clinical correlations between plasma LBP levels and survival in suspected gram-negative sepsis patients; and Example 10 relates to clinical correlations of acute phase proteins in healthy, rheumatoid arthritic and septic patients.

EXAMPLE 1

Preparation of Affinity Purified Rabbit Anti-rLBP Antibody

According to this example affinity purified rabbit anti-rLBP antibody was prepared. Specifically, rLBP (20 mg) produced according to co-owned and copending U.S. patent application Ser. No. 08/079,510 filed Jun. 17, 1993, the disclosure of which is hereby incorporated by reference was coupled to 10 mL of cyanogen bromide-activated Sepharose 4B (Sigma Chemical Co., St Louis, Mo.) in 0.2M bicarbonate, pH 8.6, containing 0.5 NaCl. Approximately 94% of the rLBP was coupled to the resin. Pooled antisera (125 mL) from two rabbits, immunized initially with $rLBP_{25}$ produced according to the methods of U.S. patent application Ser. No. 08/079,510 filed Jun. 17, 1993 and thereafter with rLBP, were diluted with an equal volume of phosphate buffered saline, pH 7.2 (PBS). A portion (50 mL) of the diluted antisera was passed through the 10 mL rLBP-Sepharose column; the column was then washed with PBS and bound antibodies were eluted with 0.1M glycine, pH 2.5. Collected fractions were immediately neutralized with 1M phosphate buffer, pH 8.0. Peak fractions were identified by measuring absorbance at 280 nm according to the method of Harlow et al., Antibodies: A Laboratory Manual, Cold Springs Harbor Laboratory Press, New York, p. 312 (1988). After several sequential column cycles, the affinity purified rabbit anti-LBP antibody was dialyzed against PBS-azide pH 7.2.

EXAMPLE 2

Preparation of Biotin Labeled Rabbit Anti-rLBP Antibody

In this example twenty milligrams of affinity purified rabbit anti-rLBP antibody produced according to the method of Example 1 was incubated with 2 mg of biotinamidocaproate N-hydroxysuccinimide ester (Sigma Chemical Co., St. Louis, Mo.) in 11 mL of 0.1M sodium bicarbonate pH 8.3 for two hours at room temperature. Unconjugated biotin was removed and the alkaline buffer exchanged by fractionating the reaction mixture on a PD-10 column (Pharmacia Biotech Inc., Piscataway, N.J.) equilibrated with PBS containing 0.1% sodium azide.

EXAMPLE 3

ELISA Procedure

Fifty microliters of affinity purified rabbit anti-rLBP antibody (2 μg/mL in PBS) were incubated overnight at 2°–8° C. (or alternatively, 1 hour at 37° C.) in the wells of Immulon 2 (Dynatech Laboratories Inc., Chantilly, Va.) microtiter plates. The antibody solution was removed and 200 μL of 1% non-fat milk in PBS (blocking agent) was added to all wells. After blocking the plates for 1 hour at room temperature, the wells were washed 3 times with 300 μL of wash buffer (PBS/0.05% Tween-20).

Standards, samples and controls were diluted in triplicate with PBS containing 1% bovine serum albumin, 0.05%

Tween 20 (PBS-BSA/Tween) and 10 units/mL of sodium heparin (Sigma Chemical Co., St. Louis, Mo.) in separate 96-well plates. rLBP or rLBP$_{25}$ standard solutions were prepared as serial two-fold dilutions from 100 to 0.012 ng/mL. Each replicate and dilution of the standards, samples and controls (50 μL) was transferred to the blocked microtiter plates and incubated for 1 hour at 37° C. After the primary incubation, the wells were washed 3 times with wash buffer. Biotin-labeled rabbit anti-LBP antibody was diluted ½000 in PBS-BSA/Tween and 50 μL was added to all wells. The plates were then incubated for 1 hour at 37° C. Subsequently, all wells were washed 3 times with wash buffer. Alkaline phosphatase-labeled streptavidin (Zymed Laboratories Inc., San Francisco, Calif.) was diluted ½000 in PBS-BSA/Tween and 50 μL was added to all wells. After incubation for 15 minutes at 37° C., all wells were washed 3 times with wash buffer and 3 times with deionized water and the chromogenic substrate p-nitrophenylphosphate (1 mg/mL in 10% diethanolamine buffer) was added in a volume of 50 μL to all wells. Color development was allowed to proceed for 1 hour at room temperature, after which 50 μL of 1N NaOH was added to stop the reaction. The absorbance at 405 nm was determined for all wells using a Vmax Plate Reader (Molecular Devices Corp., Menlo Park, Calif.).

The mean absorbance at 405 nm ($A_{405}$) for all samples and standards (in triplicate) were corrected for background by subtracting the mean $A_{405}$ of wells receiving only sample dilution buffer (no LBP) in the primary incubation step. A standard curve was then plotted as $A_{405}$ versus ng/mL of rLBP or rLBP$_{25}$. The linear range was selected, a linear regression analysis was performed and concentrations were determined for samples and controls by interpolation from the standard curve.

EXAMPLE 4

Comparative Immunoreactivity of rLBP, rLBP$_{25}$, rBPI and rBPI$_{23}$

In this example, the immunoreactivity of rLBP, rLBP$_{25}$, rBPI and rBPI$_{23}$ were compared in the BPI sandwich ELISA to determine possible immunologic cross-reactivity. Despite considerable sequence homology between LBP and BPI (see, e.g., Schumann et al., Science, 249:1429 (1990), the results illustrated in FIG. 1 show that, on a mass basis, rBPI$_{23}$ produced a signal which was approximately 3 orders of magnitude lower than that of rLBP$_{25}$ and rLBP, while rBPI produced a signal that was approximately 5 orders of magnitude lower than that of rLBP and rLBP$_{25}$. For example, a concentration of 100,000 ng/mL (100 μg/mL) of rBPI or 400 ng/mL rBPI$_{23}$ generated a signal which was equal to that produced by 0.8 ng/mL of rLBP or 0.4 ng/mL of rLBP$_{25}$. These results demonstrate minimal cross-reactivity of the antibody with BPI and confirm the specificity of the assay for LBP.

EXAMPLE 5

Measurement of rLBP Spiked into Pooled Human Plasma

In this example, the recovery of rLBP in human blood fluids was evaluated by examining pooled human plasma spiked with different concentrations of rLBP and then frozen and thawed prior to measurement in the sandwich ELISA. Recovery of spiked LBP was defined as the amount of LBP measured in spiked human plasma samples minus the concentration in the unspiked control, divided by the actual amount spiked in the sample. The fraction recovered was multiplied by 100 and the results were expressed as a percentage of the input concentration. Recovery of different concentrations of rLBP spiked into pooled human plasma samples averaged 68% and ranged from 59% at 42 μg/mL to 78% at 168 μg/mL. Table I summarizes the recovery data for each LBP spiked plasma sample.

TABLE I

Recovery of rLBP Spiked into Pooled Citrated Human Plasma

| Amount Spiked (μg/mL) | Amount Measured (μg/mL) | Amount Recovered (μg/mL) | Percent Recovery |
|---|---|---|---|
| 0 | 2.47 | — | — |
| 10.5 | 9.85 | 7.38 | 70% |
| 21 | 16.1 | 13.63 | 65% |
| 42 | 27.3 | 24.83 | 59% |
| 84 | 60.8 | 58.33 | 69% |
| 168 | 133 | 130.53 | 78% |
| | | Mean Recovery | 68% |

EXAMPLE 6

Comparison of Plasma and Serum LBP Levels

According to this example concentrations of LBP in the serum and plasma of healthy subjects were assayed and compared utilizing the sandwich ELISA assay according to Example 3. Plasma concentrations of LBP were found to be essentially the same as serum concentrations for LBP when the plasma volume was corrected for dilution (dividing by a factor of 0.85) resulting from the addition of anticoagulant. Plasma concentrations in normal human subjects were found to be 3.1 μg/mL (S.D. 0.9 μg/mL) or 3.7 μg/mL (S.D. 1.1 μl/mL) corrected, compared with 3.7 μg/mL (S.D. 0.9 μg/mL) for serum.

EXAMPLE 7

Clinical Correlations of Endogenous LBP Immunoreactivity in Human Plasma

Figure 2:
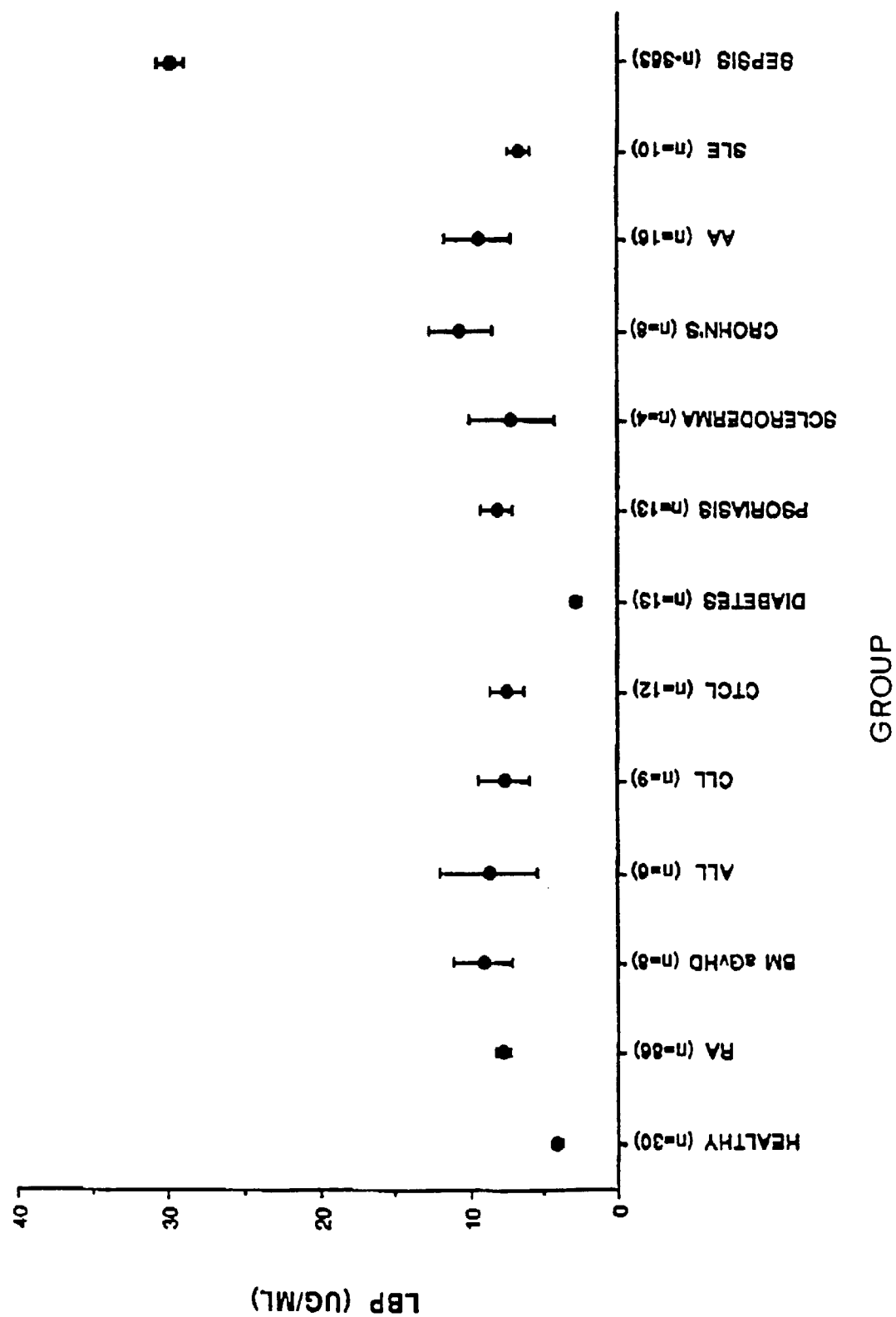
FIG. 2 depicts LBP levels (mean±standard error) in the plasma of healthy human subjects and human subjects suffering from various disease states.

In this example endogenous LBP immunoreactivity was measured in human plasma or serum samples collected from a variety of subjects suffering from gram-negative sepsis and a variety of other clinical conditions. Specifically, plasma samples of healthy individuals (59 subjects), and individuals diagnosed with gram-negative sepsis (390 subjects) were assayed for LBP levels. Serum samples of individuals with acute lymphoblastic leukemia (ALL) (6 subjects); acute graft versus host disease (aGvHD) (8 subjects); chronic lymphocytic leukemia (CLL) (9 subjects); cutaneous T-cell lymphoma (CTCL) (12 subjects); type 1 diabetes (13 subjects); aplastic anemia (AA) (16 subjects); Crohn's Disease (8 subjects); psoriasis (13 subjects); rheumatoid arthritis (RA) (86 subjects); scleroderma (4 subjects), and systemic lupus erythematosus (SLE) (10 subjects) were assayed for LBP levels. The results are shown in FIG. 2.

In another experiment, LBP immunoreactivity was also measured in plasma samples from healthy non-pregnant women (18 subjects) and in plasma samples from age-matched pregnant women in the third trimester of gestation with no evidence of active infection (18 subjects). The mean result for the healthy non-pregnant women was 3.8 μg/mL (ranging from 1.7 to 7.7 μg/mL), which was comparable to that of the healthy individuals assayed earlier, and the mean result for the pregnant women was 10.5 μg/mL (ranging from 4.6 to 22.7 μg/mL).

In a further experiment, levels of LBP as well as C-reactive protein (an acute phase protein) were measured in plasma samples from patients diagnosed with AIDS, with no concomitant infection. The mean LBP value was 5.33±2.31 µg/mL (ranging from 2.1 to 10.3 µg/mL) and the mean CRP level was 5.34±6.99 µg/mL (ranging from 0.25 to 18.3 µg/mL).

While LBP levels among subjects diagnosed as suffering from gram-negative sepsis were elevated it was found that LBP levels were not substantially elevated over normal in subjects with acute lymphoblastic leukemia, acute graft versus host disease, chronic lymphocytic leukemia, cutaneous T-cell lymphoma, type 1 diabetes, aplastic anemia, Crohn's Disease, psoriasis, rheumatoid arthritis, scleroderma, systemic lupus erythematosus (SLE), pregnancy and AIDS. Accordingly, the LBP assay of the invention is valuable for distinguishing conditions associated with endotoxin from other acute phase conditions or non-acute phase conditions not associated with endotoxin.

EXAMPLE 8

Figure 3:
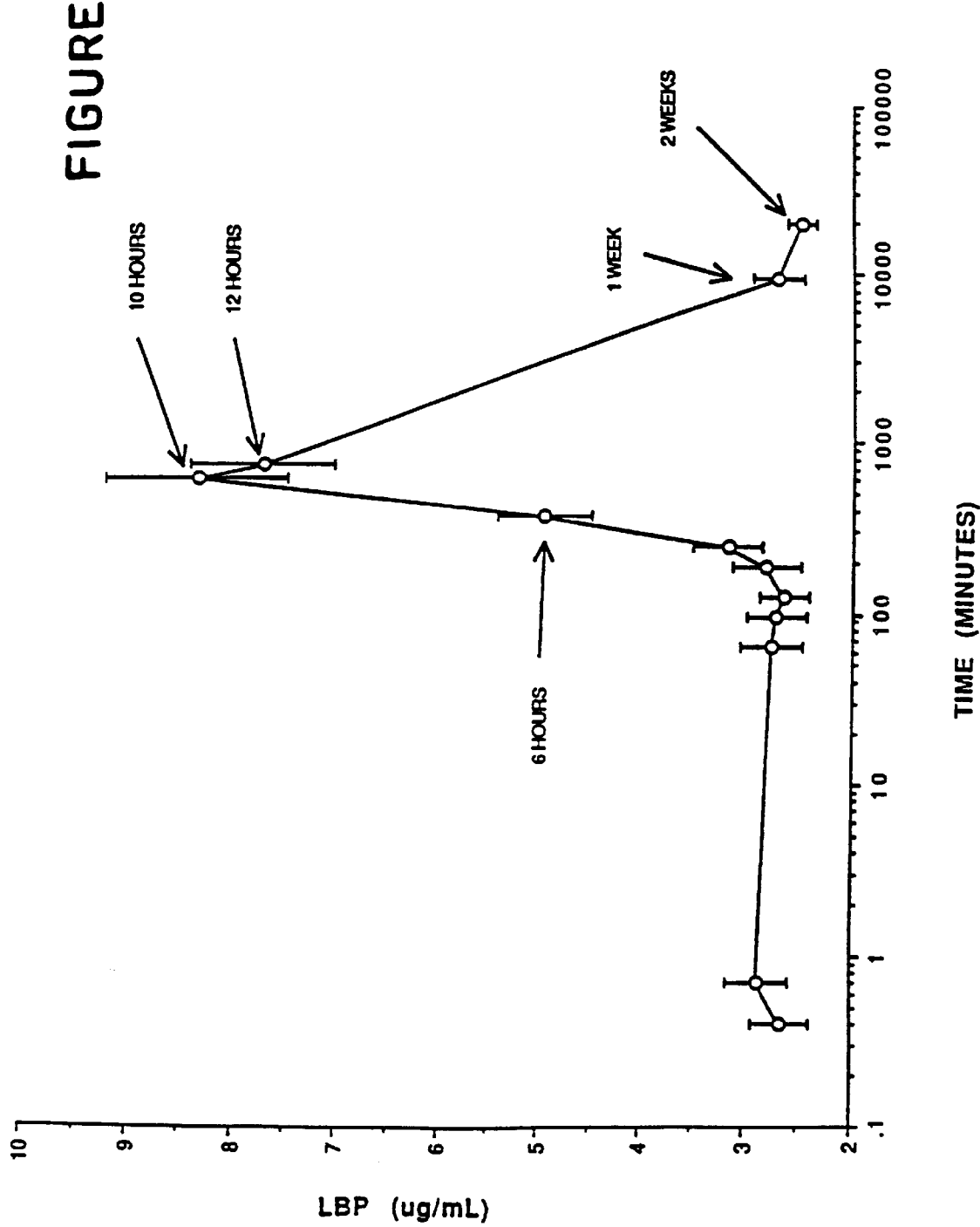
FIG. 3 depicts LBP levels (mean±standard error) in healthy subjects treated with LPS.

The Effect of LPS Administration on Endogenous LBP Levels in Healthy Subjects In this example, the effect of LPS administration on endogenous LBP immunoreactivity in healthy human subjects was determined. Specifically, healthy subjects were monitored utilizing the LBP sandwich assay for changes in LBP plasma levels at various time points after intravenous administration of 4 ng/kg LPS (16 subjects) or in control subjects (2) not receiving LPS. The results illustrated in FIG. 3 show the change in mean plasma LBP concentration with time. For those subjects treated with LPS LBP levels began to rise about 6 hours after LPS administration. Peak LBP plasma levels were observed in most subjects between 10 to 12 hours after the LPS administration. The average increase from baseline to peak LBP level was approximately 3-fold. Over this time period the mean LBP levels in control subjects remained within normal range (approximately 5 µg/mL).

It is contemplated that additional analysis will illustrate the correlation of LBP levels in body fluids with the symptoms of exposure to endotoxin and that LBP levels will be diagnostic and prognostic of disease states resulting from exposure to endotoxin.

It is contemplated that additional analysis will illustrate the correlation of LBP levels with symptoms of bacterial infections, endotoxemia and sepsis including conditions associated with sepsis including DIC and ARDS.

EXAMPLE 9

Figure 4:
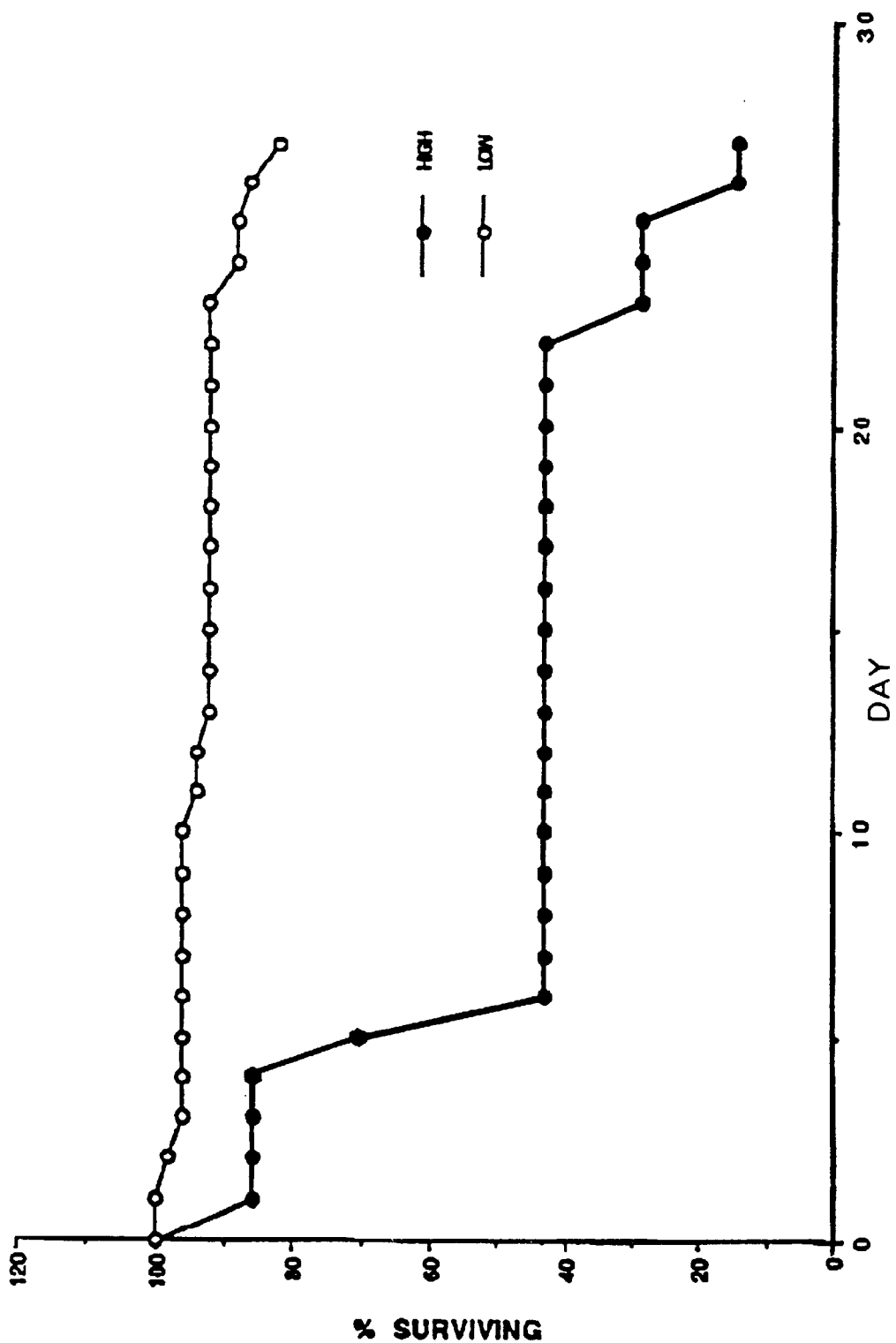
FIG. 4 depicts comparative survival in suspected gram-negative sepsis patients classified as having either high or low levels of plasma LBP.

Clinical Correlations Between Plasma LBP Levels and Survival in Suspected Gram-Negative Sepsis Patients Correlations between plasma LBP levels and survival in suspected gram-negative sepsis patients were compared using data obtained from the septic subjects described in Example 7. In this case, a standard LBP concentration was set at 46 µg/mL and patients with suspected gram-negative sepsis were classified as having either high (>46 µg/mL) or low (<46 µg/mL) LBP plasma levels as measured in pre-treatment samples. As shown in the data presented in FIG. 4, those subjects having low pretreatment plasma levels of LBP had a significantly greater survival rate (p=0.004) over a 27 day period than did those subjects having a high pretreatment plasma LBP level. These data show the utility of assaying LBP levels and comparing them to a standard LBP value for predicting the prognosis of subjects suffering from sepsis.

EXAMPLE 10

Figure 5A:
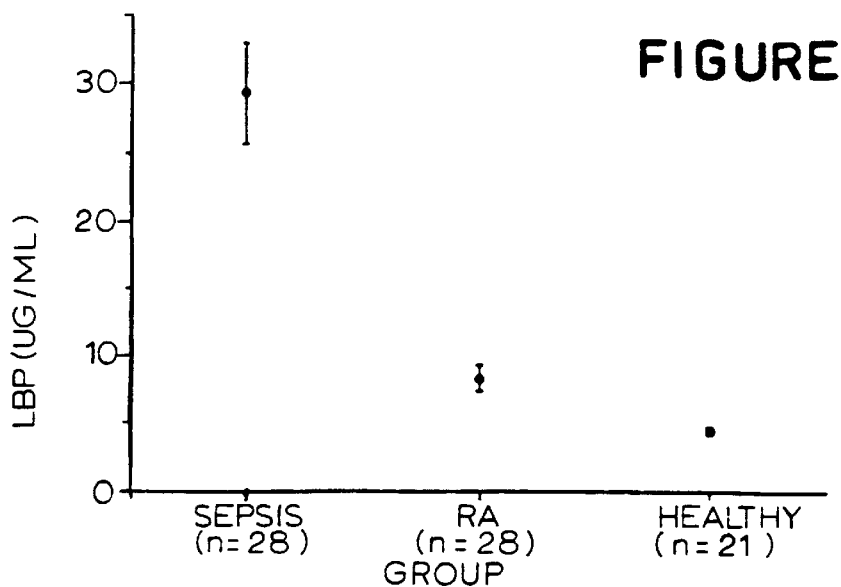
FIGS. 5a, 5b, 5c depict LBP, C-reactive protein (CRP) and fibrinogen levels (mean±standard error) in healthy, rheumatoid arthritic and septic subjects.
Figure 5B:
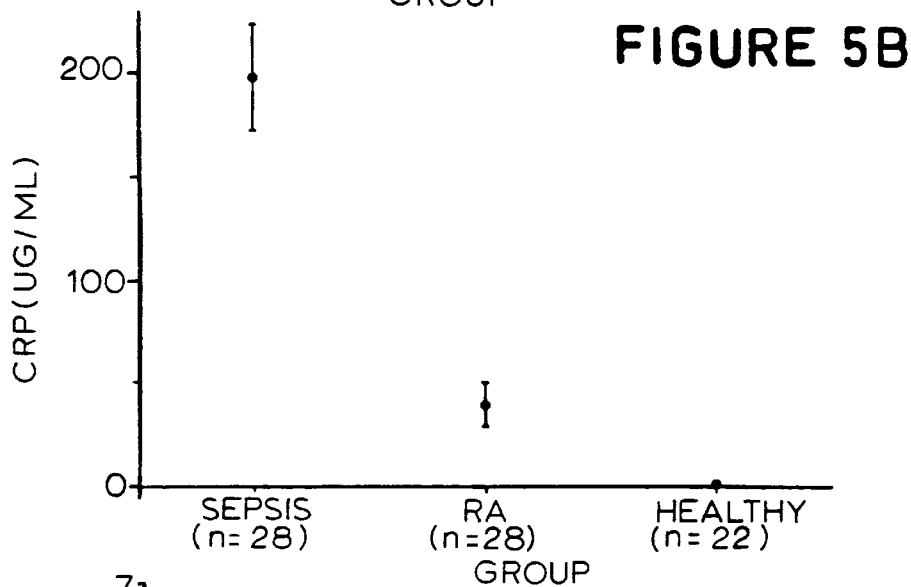
Figure 5C:
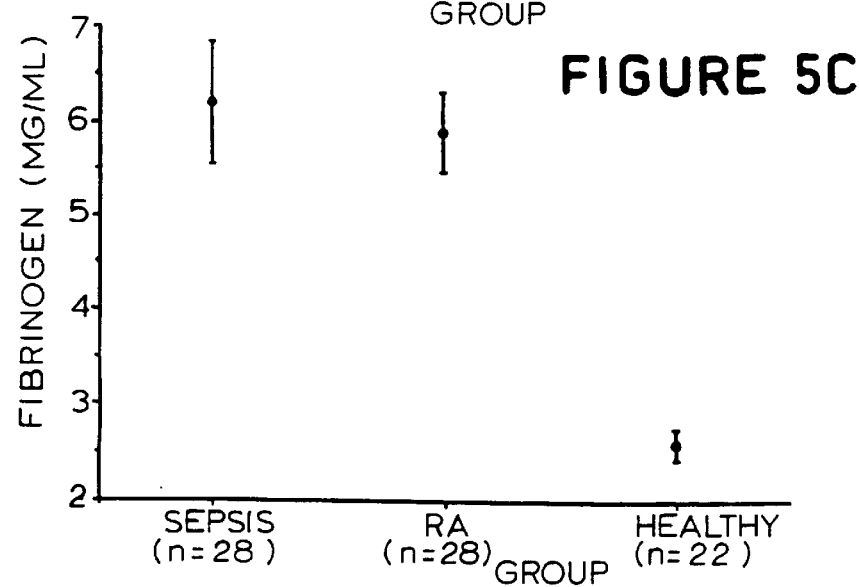

Clinical Correlations of Acute Phase Proteins in Healthy, Rheumatoid Arthritic, and Septic Patients Plasma levels of LBP, C-reactive protein (CRP) and fibrinogen were measured in small groups of healthy, rheumatoid arthritic and septic patients with the results shown in FIGS. 5a (LBP levels), 5b (CRP levels) and 5c (fibrinogen levels). The results show that relative to healthy subjects, mean fibrinogen levels were elevated approximately 2.5 fold for both rheumatoid arthritic and septic subjects. Relative to healthy subjects, mean CRP levels were found to be elevated approximately 40-fold for rheumatoid arthritic subjects and 200-fold for septic subjects. In contrast, and consistent with the results in Example 7, mean LBP levels were only slightly increased (less than 2-fold) for rheumatoid arthritis subjects while the mean LBP levels were increased by more than 6 fold for septic subjects.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

---

What is claimed is:

1. A method for specifically diagnosing exposure of a subject to endotoxin comprising the steps of determining the concentration of lipopolysaccharide binding protein (LBP) in a sample of a body fluid from the subject and correlating the concentration of LBP with a standard indicative of exposure to endotoxin, wherein LBP concentration above the standard is presumptively diagnostic of exposure of the subject to endotoxin, while a concentration below the standard is not.

2. The method of claim 1 wherein said sample is a blood sample.

3. The method of claim 1 wherein said sample is a plasma or serum sample.

4. The method of claim 1 wherein the concentration of lipopolysaccharide binding protein is determined by means of an immunoassay.

5. A method according to claim 1 wherein the standard is a concentration greater than the LBP concentration for said subject assayed during a period of pretreatment.

6. A method according to claim 1, wherein the exposure to endotoxin is indicative of an infection or endotoxin disease state.

7. A method according to claim 6, wherein the exposure to endotoxin is indicative of sepsis, including conditions associated with sepsis.

8. A method according to claim 6, wherein an elevated level of LBP is indicative of greater infection and/or endotoxemia severity.

9. A method according to claim 8, wherein an elevated level of LBP may be used to indicate the suitability of using antibiotics directed against gram-negative bacteria or other therapeutic agents targeted directly to endotoxin.

10. A method according to claim 6, wherein the standard is a concentration greater than the LBP concentration for said subject assayed during a period prior to exposure to endotoxin.

11. A method according to claim 7, wherein the standard is a concentration greater than the LBP concentration for said subject assayed during a period prior to suffering from sepsis or another condition associated with sepsis.

\* \* \* \* \*